United States Patent [19]

Inagaki et al.

[11] Patent Number: 4,734,511

[45] Date of Patent: Mar. 29, 1988

[54] METHOD FOR PRODUCING α,α-DIMETHYL-Δ-VALEROLACTONE

[75] Inventors: Takeshi Inagaki, Yokohama; Tuyoshi Irie, Chigasaki; Katsumi Nakamura, Yokohama; Denzi Sato, Tochigi, all of Japan

[73] Assignee: Nitto Chemical Industry Co., Ltd., Tokyo, Japan

[21] Appl. No.: 919,641

[22] Filed: Oct. 16, 1986

[30] Foreign Application Priority Data

Oct. 17, 1985 [JP] Japan .................................. 60-230005
Sep. 11, 1986 [JP] Japan .................................. 61-212815

[51] Int. Cl.$^4$ ............................................ C07D 309/30
[52] U.S. Cl. ..................................... 549/273; 562/602; 562/598
[58] Field of Search .......................................... 549/273

[56] References Cited

FOREIGN PATENT DOCUMENTS 616141 4/1962 Belgium .

OTHER PUBLICATIONS

Houben—Weyl, Methoden der Organischen Chemie, vol. VI/2, (1963), pp. 595–601.
T. Ikariya et al., Bull Chem. Soc. of Japan, 57 897–898, (1984).
J. L. Herrmann et al., J.C.S., Chem. Comm., (1973), 711–712.
Y. Takahashi et al., Chem. Lett., (1982), 1187–1188.
Y. Tamaru et al., J. Org. Chem., 48, 1286–1292, (1983).
Y. Ishii et al., Tetrahedron Letters, vol. 24(26), (1983), pp. 2677–2680.
Organic Syntheses, Collective, vol. 4, pp. 601–602.
I. Sircar et al., J. Med. Chem., (1983), vol. 26, pp. 1020–1027.

*Primary Examiner*—Norma S. Milestone
*Attorney, Agent, or Firm*—Cushman, Darby & Cushman

[57] ABSTRACT

A method for producing α,α-dimethyl-δ-valerolactone which comprises carrying out the addition reaction of hydrogen bromide and 2,2-dimethyl-4-pentenoic acid in the presence or absence of a catalyst to synthesize 2,2-dimethyl-5-bromovaleric acid which is then subjected to ring-closure reaction by alkali treatment.

7 Claims, No Drawings

METHOD FOR PRODUCING α,α-DIMETHYL-Δ-VALEROLACTONE

BACKGROUND OF THE INVENTION

The present invention relates to a method for producing α,α-dimethyl-δ-valerolactone, and more particularly, to a method for producing α,α-dimethyl-δ-valerolactone which is useful as a material for compounds having a

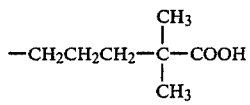

group such as Lopid (produced by Parke Davis, U.S.A.) represented by the formula,

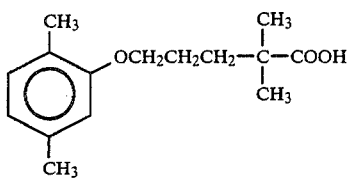

etc. which are used as anti-arteriosclerotic agents and anti-hyperproteotic agents.

Hitherto, for the production of α,α-dimethyl-δ-valerolactone (hereinafter referred to as DVL), the following methods are known:

(1) A method of reducing 2,2-dimethylglutaric acid anhydride.

2,2-Dimethylglutaric acid anhydride, a material for this method, is synthesized through steps as many as Michael addition reaction, hydrolysis, oxidation and lactonization using isobutylaldehyde and acrylonitrile as starting materials, and also its yield is low. Besides, reduction of said acid anhydride has a defect that it requires a ruthenium catalyst which is complicated and not readily available, and also that its yield is low [Bull. Chem. Soc. Jpn. 57, 897 (1984)].

(2) A method of alkylating δ-valerolactone with methyl iodide and diisopropyllithium amide.

This method has a defect that both δ-valerolactone and diisopropyllithium amide are so expensive that the resultant product is also expensive [J. C. S., Chem. Comm. (1973), 711].

(3) A method of treating 4-methyl-1,4-pentanediol with 97–100% sulfuric acid and 100% formic acid or with 97–100% sulfuric acid, copper oxide and carbon monoxide, followed by reaction with water.

4-Methyl-1,4-pentanediol, a material for this method, is produced by reacting γ-butyrolactone with methyl bromide in the presence of magnesium, but this reaction has a defect that its yield is so low that the yield of the resulting α,α-dimethyl-δ-valerolactone is also low [Chem. Lett. (1982), 1187].

(4) A method of oxidizing 2,2-dimethyl-1,5-pentanediol using allyl halide and a palladium catalyst.

2,2-Dimethyl-1,5-pentanediol, a material for this method, is synthesized by reduction of the diester or acid anhydride of 2,2-dimethylglutaric acid. Synthesis of said diester or acid anhydride is not easy as described in the conventional method (1), and besides LiAlH₄, etc. are used for said reduction, so that the process becomes troublesome and expensive. Further, this method has a defect that, since the isomeric lactone as shown below is produced as by-product in the lactonization, the selectivity of DVL is low [J. Org. Chem., 48, 1286 (1983)]:

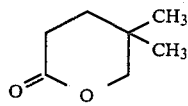

(5) A method of dehydrogenating 2,2-dimethyl-1,5-pentanediol into a lactone using a ruthenium catalyst.

2,2-Dimethyl-1,5-pentanediol, a material for this method, is not readily available as described in the conventional method (4). Also, the lactonization has a defect that it produces the isomeric lactone as shown above, lowering the selectivity of DVL [Tetrahedron Lett., 24, 2677 (1983)].

(6) A method of reacting 2,2-dimethylvinylbutyric acid ester with cobalt carbonyl.

In this method, a highly poisonous reagent such as cobalt carbonyl is used, and also the reaction is carried out at a temperature as high as 240° C. and a pressure as high as 290 atm., and therefore, there is a defect that a high-temperature high-pressure apparatus is necessary and besides the operation is difficult (Belgian Patent No. 616,141).

As described above, the conventional methods have defects that access to or synthesis of both raw materials and reaction reagents is so difficult that the desired α,α-dimethyl-δ-valerolactone becomes expensive, the reaction yield is low, and that the selectivity of DVL is so low that the isomer is produced in large amounts. Consequently, a synthetic method for DVL suitable for industrialization has not yet been established.

The present invention was made to solve the defects of the conventional methods, and its object is to provide a method for producing DVL with ease, in high yields and economically using easily available materials alone without using special and expensive chemicals.

The present inventors have extensively studied to attain the foregoing objects, and as a result, found that DVL can be obtained easily and in high yields by carrying out the addition reaction of hydrogen bromide and 2,2-dimethyl-4-pentenoic acid (hereinafter referred to as DMP) in the presence or absence of a catalyst to synthesize 2,2-dimethyl-5-bromovaleric acid which is then treated with an alkali, said 2,2-dimethyl-4-pentenoic acid used as a material being easily obtained by heating allyl isobutyrate in the presence of sodium hydride or lithium hydride.

There are two routes in the method of the present invention. One route is one in which addition of hydrogen bromide to DMP is carried out in the presence of a radical initiator, which is a catalyst, to synthesize 2,2-dimethyl-5-bromovaleric acid which is then treated with an alkali. By this method, the desired DVL can be obtained in high yields. The other route is one in which 2,2-dimethyl-4-pentenoic acid is added to an organic solvent containing hydrogen bromide previously absorbed and dissolved to cause hydrogen bromide to add to said acid, and the resulting 2,2-dimethyl-5-bromovaleric acid is then treated with an alkali. By this method, DVL can be produced easily and in high yields.

The method of the present invention has excellent effects as described below:

(1) DMP easily obtainable from allyl isobutyrate is used as a material and DVL is obtained from it in high yields, so that DVL can be obtained easily and cheaply.

(2) When addition of hydrogen bromide is carried out particularly using no catalyst, by-products such as a five-membered cyclic lactone as described below are not formed, and also there is no contamination of DVL with the catalyst and decomposition products thereof. Purification of DVL is therefore so simple that high-purity DVL can be produced:

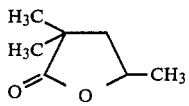

The process of synthesis according to the present invention will be shown below in flow sheet:

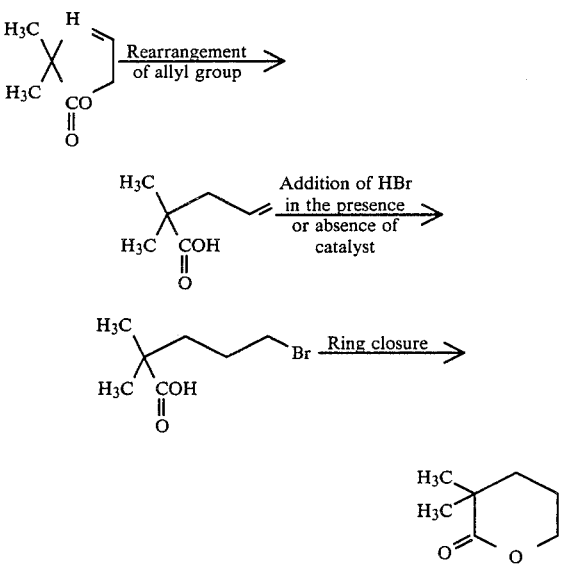

DMP, a material used in the present invention, is easily obtained by the rearrangement of the allyl group of allyl isobutyrate. Specifically, DMP is produced as follows: To a reactor are added a solvent and sodium hydride or lithium hydride of 1.0 to 1.6 times by mole based on allyl isobutyrate, and the mixture is heated with stirring at a temperature of from 80° to 130° C., preferably from 110° to 120° C.; subsequently, allyl isobutyrate is added dropwise over 1 to 8 hours, the reaction mixture is aged with stirring and heating at a temperature of from 80° to 130° C. for 1 to 5 hours, and after cooling, methanol and water are added to stop the reaction; the reaction solution is separated into a solvent and aqueous layers, and the aqueous layer is acidified to a pH of 1 with hydrochloric acid to liberate DMP which is then extracted with an organic solvent and isolated by distillation, etc.

The solvent used in the rearrangement step includes for example benzene, toluene, dioxane, etc. The solvent used for the extraction of DMP includes for example benzene, toluene, hexane, ethyl acetate, chloroform, ethyl ether, etc.

What is essential to the present invention is radical addition of hydrogen bromide to DMP, in other words, the bromine atom should add to the terminal (5-position) of DMP. When the bromine atom adds to the 4-position, the addition product unpreferably produces the five-membered cyclic lactone, a by-product, upon alkali treatment.

There are two methods for the radical addition of hydrogen bromide. One of them is the addition of hydrogen bromide to DMP in the presence of a catalyst. A solvent, DMP and a radical initiator are charged into a reaction vessel. Thereto, 1 to 1.5 times by mole based on DMP of hydrogen bromide gas are bubbled for 1 to 5 hours. After the completion of bubbling, the resulting reaction mixture are subjected to ageing to complete the reaction for 1 to 5 hours. The reaction is carried out at a temperature of $-10°$ C. to 70° C., however, it is preferred to carry out at a lower temperature such as $-10°$ to 40° C. in order to reduce side reactions as much as possible.

In case of this addition reaction, it is preferred to carry out the addition in a homogeneous system using an organic solvent.

For the organic solvent, any of aliphatic hydrocarbons, aromatic hydrocarbons, ethereal solvents and halogen-containing solvents will do, so far as they will dissolve DMP and the radical initiator, but not react with hydrogen bromide. The amount of the solvent used is 1 to 20 times by weight based on DMP. Specific examples of the solvent include for example hexane, pentane, ether, toluene, carbon tetrachloride, benzene, dioxane, tetrahydrofuran (THF), acetic acid, etc.

For the catalyst, organic peroxides or organic azo compounds normally used for radical polymerization, etc. may be used. The amount of the catalyst used is 0.05 to 5 wt. %, preferably 0.1 to 2 wt. % based on DMP. Specific examples of the catalyst include for example di-tert-butyl peroxide, tert-butylcumyl peroxide, dicumyl peroxide, benzoyl peroxide, isobutyryl peroxide, propionyl peroxide, tert-butyl hydroperoxide, cumene hydroperoxide, diisopropylbenzene hydroperoxide, para-menthane hydroperoxide, tert-butyl peroxybenzoate, diisopropyl peroxycarbonate, azobisisobutyronitrile, etc.

The other method for the addition of hydrogen bromide to DMP is one in which DMP, dissolved in a small amount of a solvent, is added to a solvent containing hydrogen bromide previously absorbed of 0.5 to 1.5 times by mole based on DMP, in the absence of a catalyst, and the mixture is aged at a temperature of from $-30°$ to 50° C. for 0.5 to 5 hours. The solvent used includes for example hexane, pentane, ether, toluene, carbon tetrachloride, benzene, dioxane, tetrahydrofuran (THF), acetic acid, etc.

The amount of the solvent for dissolving hydrogen bromide is 1 to 25 times by weight, preferably 8 to 20 times by weight based on DMP. For the solvent for dissolving DMP in order to add DMP to the hydrogen bromide solution, the same solvent as used to dissolve hydrogen bromide is preferred in terms of solvent recovery. The amount of the solvent used is 1 to 5 times by weight, preferably 1 to 3 times by weight based on DMP.

With the method of adding DMP to the solution of hydrogen bromide in the solvent, there is no formation of the five-membered cyclic lactone as by-product.

In the latter method, the addition of hydrogen bromide to the 5-position is easily carried out without using a radical initiator (e.g. peroxides) as a catalyst. Because of this, there is no need to remove the catalyst or decomposition products thereof after completion of the reaction, so that purification is easy. In addition, there is no need for attention necessary to handle peroxide catalysts, so that operation is easy. This latter method is therefore more preferred than the former one in these respects.

2,2-Dimethyl-5-bromovaleric acid (hereinafter referred to as DMBr) obtained by this hydrogen bromide addition produces DVL by its ring closure upon treatment with an alkali.

The alkali treatment is carried out by adding to DMBr a 5 to 50% aqueous alkali solution containing an alkali of 1.0 to 3.0 times by mole based on DMBr, and stirring the mixture at a temperature of from 0° to 50° C. for 0.5 to 3 hours. After reaction, on adding hydrochloric acid to the reaction solution to a pH of 1, the reaction solution is separated into DVL and an aqueous layer, DVL being thus obtained.

The alkali used for alkali treatment includes for example the hydroxides and carbonates of alkali metals such as sodium hydroxide, potassium hydroxide, sodium carbonate, potassium carbonate, etc. A required amount of the alkali is at least 1.0 time by mole based on DMBr, and generally 1.0 to 3.0 times by mole, preferably 1.1 to 2.0 times by mole is used.

DVL thus obtained is of high purity, but when DVL of higher purity is required, purification by distillation will suffice.

The method of the present invention will be illustrated specifically with reference to the following examples, but it is not limited to these examples.

EXAMPLE 1

To a four-necked flask equipped with a stirrer, thermometer and condenser were added 64 g of 2,2-dimethyl-4-pentenoic acid and 300 cc of benzene, a solvent, and the acid was dissolved in benzene with stirring.

0.5 Gram of benzoyl peroxide was added, and 43 g of a hydrogen bromide gas was bubbled into the solution at room temperature over 2 hours with stirring. After completion of bubbling, stirring was continued for 2 hours, and the reaction solution was then washed with water to separate the benzene layer. The benzene layer was concentrated under reduced pressure to recover 204 g of benzene, and 106 g of the oily residue was obtained.

200 Grams of a 10% aqueous sodium hydroxide solution was added to the residue to make the mixture weakly alkaline, and the mixture was extracted with addition of 100 cc of benzene. Activated carbon was added to the aqueous layer, and after filtration, hydrochloric acid was added to the filtrate to a pH of 4.0, followed by extraction with benzene. This benzene extract was freed of benzene by distillation, and the resulting concentrated solution was distilled under reduced pressure.

Initial fraction (~108° C./20 mmHg)—9 g
Main fraction (108°–113° C./20 mmHg)—42.9 g The main fraction obtained was confirmed to be DVL by nuclear magnetic resonance analysis. $^1$H-NMR (270 MHz, CDCl$_3$):

δ(ppm) 1.30(3H, s, CH$_3$×2), 1.77(2H, t, 4-H), 1.92(2H, m, 5-H), 4.35(2H, t, H-6).

The yield of DVL was found to be 66.7% (purity, 97.2%) by gas-chromatographic analysis.

EXAMPLE 2

Procedure was carried out in the same manner as in Example 1 except that 270 g of a 10% aqueous sodium carbonate solution was used in place of the 10% aqueous sodium hydroxide solution. The yield of DVL was 70.5% (purity, 97.4%).

EXAMPLE 3

According to the method of Example 1, 10 g of 2,2-dimethyl-4-pentenoic acid was reacted with 7.15 g of dry hydrogen bromide in 100 cc of hexane in the presence of 100 mg of benzoyl peroxide. The yield of DVL was 86.4% (purity, 98.0%).

EXAMPLE 4

Procedure was carried out in the same manner as in Example 3 except that 100 mg of azobisisobutyronitrile was used in place of benzoyl peroxide. The yield of DVL was 88.5% (purity, 97.5%).

EXAMPLE 5

Procedure was carried out in the same manner as in Example 4 except that the amount of azobisisobutyronitrile was changed to 1.0 g, to obtain DVL. The yield of DVL was 90.0% (purity, 98.0%).

EXAMPLE 6

Procedure was carried out in the same manner as in Example 1 except that 350 g of a 10% aqueous potassium carbonate solution was used in place of the 10% aqueous sodium hydroxide solution. The yield of DVL was 85.7% (purity, 95.7%).

EXAMPLE 7

To the reactor used in Example 1 were added 10 g of DMP and 100 ml of hexane, and after adding 100 mg of benzoyl peroxide, a hydrogen bromide gas was bubbled into the solution at a rate of 0.15 g/min at room temperature for 1 hour with stirring. After completion of bubbling, stirring was continued for 2 hours to carry out ageing. Thereafter, ring closure was carried out by treatment with 10 ml of a 10% aqueous sodium carbonate solution in the same manner as in Example 2. The yield of DVL was 85.3%.

EXAMPLE 8

To a four-necked flask equipped with a stirrer, thermometer and condenser was added 100 ml of hexane, and cooled to −25° C. Thereafter, 6.70 g of a hydrogen bromide gas was bubbled and absorbed into the hexane while shading the light. After adding a solution of 10 g of DMP in 15 ml of hexane to this solution at −25° C. while shading the light, ageing was carried out for 3 hours with stirring while allowing the temperature to gradually rise to room temperature. Thereafter, the reaction solution was concentrated under reduced pressure, 80 ml of a 10% aqueous sodium carbonate solution was added to 17.31 g of the oily concentrate thus obtained, and stirring was continued at room temperature for 3 hours to complete ring closure. To the resulting reaction solution was added 10 ml of conc. hydrochloric acid to make the pH 1, followed by extraction with chloroform, drying and concentration under reduced pressure.

Thus, 9.90 g of DVL (yield, 99.0%, purity, 97.7%) was obtained. Purification of this DVL by distillation gave a high-purity DVL (99.5%; b.p., 108°–113° C./20 mmHg).

EXAMPLE 9

To a four-necked flask equipped with a stirrer, thermometer and condenser were added 40.6 g of 60% sodium hydride and 50 ml of toluene, and the resulting mixture was heated to 110° C. with stirring. Thereafter, 100 g of allyl isobutyrate was added dropwise over 5 hours, and after addition, stirring was continued at 110° C. for further 3 hours.

After completion of the reaction, the reaction solution was cooled to room temperature, and 18 ml of methanol was added to decompose unreacted sodium hydride. After dissolving insoluble matters with addition of 200 ml of water, the toluene and aqueous layers were separated from each other.

The separated aqueous layer was acidified to a pH of 1 with conc. hydrochloric acid, and the formed oily layer was recovered. The aqueous layer was extracted with toluene, and the toluene extract and the oily layer recovered above were combined, concentrated and distilled under reduced pressure to obtain DMP.

Initial fraction (~65° C./2 mmHg)—2.7 g
Main fraction (65°-73° C./2 mmHg)—85.5 g 85.5 Grams of this DMP was dissolved in 145 ml of hexane, added at room temperature to a solution of 58.5 g of hydrogen bromide in 1500 ml of hexane and aged as such at room temperature for 2 hours with stirring.

In the same manner as in Example 8, ring closure was carried out by treatment with 680 ml of a 10% aqueous sodium carbonate solution. The amount of DVL obtained was 82.9 g (yield based on allyl isobutyrate, 82.9%) (purity, 96.5%).

EXAMPLE 10

To the reactor used in Example 8 was added 100 ml of hexane, and 3.55 g of hydrogen bromide was bubbled and absorbed into the hexane at 0° C. To this solution, a solution of 5.00 g of DMP in 10 ml of hexane was added dropwise at 0° C. over 15 minutes, and subsequently, ageing was carried out for 3 hours with stirring while allowing the temperature to gradually rise to room temperature.

Thereafter, in the same manner as in Example 8, treatment with 50 ml of a 10% aqueous sodium carbonate solution was carried out to obtain 4.97 g of DVL (yield, 99.3%; purity, 99.2%).

EXAMPLE 11

To the reactor used in Example 8 was added 100 ml of hexane, and 4.5 g of hydrogen bromide was bubbled and absorbed into the hexane at −20° C. To this solution, a solution of 7.00 g of DMP in 10 ml of hexane was added at a time at −20° C., and subsequently, ageing was carried out for 3 hours with stirring while allowing the temperature to gradually rise to room temperature.

Thereafter, in the same manner as in Example 8, treatment with 65 ml of a 10% aqueous sodium carbonate solution was carried out to obtain 6.73 g of DVL (yield, 96.1%; purity, 97.3%).

EXAMPLE 12

A solution of 10 g of DMP in 15 ml of hexane was added dropwise to 100 ml of hexane containing 4.40 g of hydrogen bromide at 0° C. at a rate of 0.5 ml/min over about 60 minutes, during which hydrogen bromide was bubbled into the hydrogen bromide solution at a rate of 0.15 g/min while shading the light. Bubbling of hydrogen bromide was stopped simultaneously with completion of the addition, and the reaction solution was stirred for 45 minutes while allowing its temperature to gradually rise from 0° C. to 18° C. Thereafter, in the same manner as in Example 8, treatment with 80 ml of a 10% aqueous sodium carbonate solution was carried out to obtain 9.75 g of DVL (yield, 97.5%; purity, 97.2%).

What is claimed is:

1. A method for producing $\alpha,\alpha$-dimethyl-$\delta$-valerolactone which comprises adding 2,2-dimethyl-4-pentenoic acid to an organic solvent containing hydrogen bromide previously dissolved to carry out the addition reaction of hydrogen bromide and said acid to synthesize 2,2-dimethyl-5-bromovaleric acid, and subjcting 2,2-dimethyl-5-bromovaleric acid to ring-closure reaction by alkali treatment.

2. A method for producing $\alpha,\alpha$-dimethyl-$\delta$-valerolactone according to claim 1, wherein the amount of hydrogen bromide dissolved in the organic solvent is 0.5 to 1.5 times by mole based on 2,2-dimethyl-4-pentenoic acid.

3. A method for producing $\alpha,\alpha$-dimethyl-$\delta$-valerolactone according to claim 2, wherein the amount of the organic solvent for dissolving hydrogen bromide is 1 to 25 times by weight based on 2,2-dimethyl-4-pentenoic acid.

4. A method for producing $\alpha,\alpha$-dimethyl-$\delta$-valerolactone according to claim 5, wherein the amount of the organic solvent for dissolving hydrogen bromide is 8 to 20 times by weight based on 2,2-dimethyl-4-pentenoic acid.

5. A method for producing $\alpha,\alpha$-dimethyl-$\delta$-valerolactone according to claim 1, wherein said alkali treatment is carried out with an alkali selected from the group consisting of the hydroxides or carbonates of alkali metals.

6. A method for producing $\alpha,\alpha$-dimethyl-$\delta$-valerolactone according to claim 5, wherein said alkali is sodium carbonate.

7. A method for producing $\alpha,\alpha$-dimethyl-$\delta$-valerolactone according to claim 1, wherein 2,2-dimethyl-4-pentenoic acid is obtained by heat-treating allyl isobutyrate in the presence of sodium hydride or lithium hydride.

* * * * *